(12) United States Patent
Huber et al.

(10) Patent No.: US 9,851,303 B2
(45) Date of Patent: Dec. 26, 2017

(54) SYSTEM AND METHOD FOR INDUCING AND DETECTING MULTI-PHOTON PROCESSES IN A SAMPLE

(71) Applicant: Ludwig-Maximilians-Universität München, München (DE)

(72) Inventors: Robert Alexander Huber, Lübeck (DE); Sebastian Karpf, Munich (DE); Matthias Eibl, Witzmannsberg (DE)

(73) Assignee: Ludwig-Maximilians-Universität München, München (DE)

( * ) Notice: Subject to any disclaimer, the term of this patent is extended or adjusted under 35 U.S.C. 154(b) by 0 days.

(21) Appl. No.: 15/316,568

(22) PCT Filed: Jun. 3, 2015

(86) PCT No.: PCT/EP2015/062371
§ 371 (c)(1),
(2) Date: Dec. 6, 2016

(87) PCT Pub. No.: WO2015/185620
PCT Pub. Date: Dec. 10, 2015

(65) Prior Publication Data
US 2017/0146458 A1 May 25, 2017

(30) Foreign Application Priority Data

Jun. 6, 2014 (EP) .................................. 14001980
Nov. 7, 2014 (EP) .................................. 14192304

(51) Int. Cl.
*G01N 21/64* (2006.01)
*G01N 21/65* (2006.01)

(52) U.S. Cl.
CPC ..... *G01N 21/6456* (2013.01); *G01N 21/6408* (2013.01); *G01N 21/65* (2013.01);
(Continued)

(58) Field of Classification Search
CPC ....... G01N 2021/6484; G01N 21/6408; G01N 21/6456; G01N 21/65; G01N 2201/06146;
(Continued)

(56) References Cited

U.S. PATENT DOCUMENTS

2005/0057736 A1* 3/2005 Tani .................... G03F 7/70375
355/55
2007/0229946 A1* 10/2007 Okada ................ G01N 21/6458
359/385
(Continued)

OTHER PUBLICATIONS

Haderka et al., "Experimental multi-photon-resolving detector using a single avalanche photodiode." *The European Physical Journal D-Atomic, Molecular, Optical and Plasma Physics* 28.1 (2004): 149-154.
(Continued)

*Primary Examiner* — Mark R Gaworecki
(74) *Attorney, Agent, or Firm* — Sunstein Kann Murphy & Timbers LLP

(57) ABSTRACT

Described is a system for inducing and detecting multi-photon processes, in particular multi-photon fluorescence or higher harmonic generation in a sample. The system comprises a dynamically-controllable light source, said dynamically-controllable light source comprising a first sub-light source, said first sub-light source being electrically controllable such as to generate controllable time-dependent intensity patterns of light having a first wavelength, and at least one optical amplifier, thereby allowing for active time-control of creation of multi-photon-excitation. The system further comprises a beam delivery unit for delivering light generated by said dynamically-controllable light source to a sample site, and a detector unit or detector assembly for detecting signals indicative of said multi-photon process, in particular multi-photon fluorescence signals or higher harmonics signals.

20 Claims, 11 Drawing Sheets

(52) U.S. Cl.
CPC ......... *G01N 2021/6484* (2013.01); *G01N 2201/0635* (2013.01); *G01N 2201/06146* (2013.01); *G01N 2201/105* (2013.01); *G01N 2201/11* (2013.01); *G01N 2201/12* (2013.01)

(58) Field of Classification Search
CPC ..... G01N 2201/0635; G01N 2201/105; G01N 2201/11; G01N 2201/12
See application file for complete search history.

(56) References Cited

U.S. PATENT DOCUMENTS

| | | |
|---|---|---|
| 2008/0198445 A1 | 8/2008 | Murison et al. |
| 2008/0205833 A1 | 8/2008 | Fu et al. |
| 2011/0044910 A1 | 2/2011 | Lin et al. |

OTHER PUBLICATIONS

Rowen et al., "A combined Yb-Raman fiber amplifier for generating narrow linewidth, high-power pulses in the 1100-1200 nm wavelength range and efficient nonlinear conversion into yellow." *SPIE LASE*. International Society for Optics and Photonics, 2013.

Karpf et al. "Time-Encoded Raman: Fiber-based, hyperspectral, broadband stimulated Raman microscopy", May 16, 2014 (May 16, 2014), XP055183803, Retrieved from the Internet: URL:http://arxiv.org/abs/1405.4181.

International Search Report and Written Opinion in International Application No. PCT/EP2015/062371 dated Aug. 7, 2015, 12 pages.

* cited by examiner

SYSTEM AND METHOD FOR INDUCING AND DETECTING MULTI-PHOTON PROCESSES IN A SAMPLE

CROSS-REFERENCE TO RELATED APPLICATIONS

This Application is a U.S. national stage entry under 35 USC §371 of PCT/EP2015/062371 filed Jun. 3, 2015, which claims priority to European Patent Application 14001980.3, filed Jun. 6, 2014, and to European Patent Application 14192304.5, filed Nov. 7, 2014; all of which are incorporated herein by reference in their entireties.

FIELD OF THE INVENTION

The present invention is in the field of optics. In particular, the present invention relates to a system and a method for inducing and detecting multi-photon processes in a sample.

BACKGROUND OF THE INVENTION

Such multi-photon processes may involve the simultaneous absorption of two photons. A well-known example is multi-photon fluorescence or higher harmonic generation.

A well-known application is the so-called two-photon excitation microscopy. In two-photon excitation microscopy, a fluorophore is excited by the absorption of two photons simultaneously in one quantum event. Each photon carries approximately half the energy necessary to excite the fluorophore. An excitation then results in the subsequent emission of a fluorescence photon with an energy that is typically higher than that of either of the two excitation photons.

Since the probability of the simultaneous absorption of two photons is very low, high excitation intensities are needed, which in practice are provided by femtosecond lasers which deliver a passively-controlled sequence of very short pulses.

Commercially-available femtosecond lasers are expensive. Also, commercially-available femtosecond lasers are not easy to integrate into other imaging modalities.

In Sebastian Karpf et al., "*Time-encoded Raman: Fiber-based, hyperspectral, broadband stimulated Raman microscopy*" http://arxivorg/abs/1405.4181, a time-encoded Raman setup using a Fourier Domain Mode-Locked (FDML) laser source together with a dynamically-controllable light source as Raman-pump source is disclosed. The time-encoded Raman setup includes a differential balanced photodetector for detecting a stimulated Raman gain signal. The differential balance photodetector includes InGaAs diodes for receiving near infrared light with a wavelength of more than 1200 nm. This detector is not suitable for detecting signals indicative of a multi-photon process, such as a multi-photon fluorescence signal or a higher harmonics signal.

SUMMARY OF THE INVENTION

It is thus one object underlying the invention to provide a system and a method for inducing and detecting multi-photon processes that overcome the above drawbacks. This object is solved by a system according to claim 1, a system according to claim 14 as well as a method according to claim 15. Preferable embodiments are defined in the dependent claims.

According to the invention, the system comprises
  a dynamically-controllable light source, said dynamically-controllable light source comprising
    a first sub-light source, said first sub-light source being electrically controllable such as to generate controllable time-dependent intensity patterns of light having a first wavelength, and
    at least one optical amplifier,
  thereby allowing for active time-control of creation of multi-photon-excitation,
  a beam delivery unit for delivering light generated by said dynamically-controllable light source to a sample site and
  a detector unit or detector assembly for detecting signals indicative of said multi-photon process, in particular multi-photon fluorescent signals or higher harmonics signals.

The dynamically-controllable light source may in particular be a coherent narrow-band dynamically-controllable light source. Further, the multi-photon process may be a two-photon or three-photon process.

By using a dynamically-controllable light source, as compared to a passively-pulsed laser source such as an ordinary femtosecond laser, the system becomes much more flexible and allows for many new applications. In particular, it allows for a much better integration in systems using additional imaging modalities or adaption to desired experimental setups.

In a preferred embodiment, the dynamically-controllable light source and the detector unit/assembly are adapted to communicate or share timing, time control or time sensing information in at least one direction, and in particular by
  a trigger signal exchanged at least in one direction,
  sharing common electrical signals, in particular the same time gate or a sample clock,
  synchronizing or phase-locking electrical signals involved in the time control of the dynamically-controllable light source and the detector unit/assembly.

As will become apparent from the description of the specific embodiments below, allowing to share or exchange timing information between the dynamically-controllable light source and the detector greatly increases the usefulness, versatility and flexibility of the system.

Preferably, the dynamically-controllable light source is a coherent dynamically-controllable light source, in particular a narrow-band coherent dynamically-controllable light source.

In a preferred embodiment, said multi-photon process is a two-photon or three-photon process, and/or the multi-photon process involves a simultaneous absorption of at least two photons.

In a preferred embodiment, the system comprises a time control unit for controlling one or both of the dynamically-controllable laser and the detection unit/assembly.

Preferably, the system comprises an electronic function generator generating electronic signals for operation of one or both of the dynamically-controllable light source and the detector unit/assembly, and in particular to an analog-to-digital converter of the detector, wherein the electronic function generator is preferably synchronized with the dynamically-controllable light source.

In a preferred embodiment, the system is part of an endoscope, an OCT device, a light microscope, a photoacoustic imaging device, a Raman spectrometer or an ultrasonic imaging device.

Preferably, said system comprises a device for scanning different sample locations.

In a preferred embodiment, the device for scanning different sample locations comprises
- one or more moving mirrors for deflecting light from said dynamically-controllable light source to a predetermined sample location and/or one or more mirrors for deflecting the light reflected from a sample location,
- a device for scanning an optical fiber or a fiber bundle carrying light of said dynamically-controllable light source with respect to a sample or
- a device for scanning the sample relative to the light signal.

In a preferred embodiment, the system is further adapted for fluorescence lifetime imaging.

Preferably, said beam delivery unit comprises an optical fiber, wherein at least 50%, preferably at least 80%, and most preferably at least 90% of the light path between the dynamically-controllable light source and the sample site is located in said optical fiber, and/or wherein the optical fiber is preferably a single mode optical fiber and in particular a polarization maintaining fiber.

In a preferred embodiment, the detector unit/assembly comprises at least one photo detector, wherein at least one photo detector is preferably an avalanche photo diode, a photo-multiplier-tube, a multi-channel-plate, or an avalanche photo diode array.

Preferably, the output signal of said photo detector is connected to an analog-digital-converter, in particular an analog-digital-converter on a personal computer, wherein the signal detection by means of the analog-digital-converter is preferably synchronized with the dynamically-controllable light source, in particular to establish a time-gated detection to suppress background signals at times when no signal is expected. By averaging such time-gated signals the dynamic range of signal intensities can be enhanced up to an ideal square root behavior.

In a preferred embodiment, the optical signals created by or indicative of said multi-photon process is deflected to said detector unit or detector assembly using free space optics.

Preferably, said signal created by or indicative of said multi-photon process is collected with and guided to the detector unit/assembly with an optical fiber, in particular a multi-mode fiber.

In a preferred embodiment, the beam delivery unit comprises a single mode core of a double clad fiber, and in which signals generated by or indicative of said multi-photon process are guided through the multi-mode cladding to the detector unit/assembly, and/or further comprising one or more dichroic filters, or other wavelength selective elements to separate the light signal for inducing multi-photon processes and the light signal generated by or indicative of said multi-photon process from each other.

Preferably, the system is a device for multi-modal measurements combining the measurement of the multi-photon processes with at least one other measurement modality, in particular light microscopes, confocal microscopes, OCT, Raman spectroscopy or different modes of multi-photon processes, wherein the multi-modal measurements are encoded sequentially in time, thereby allowing to detect different measurement or imaging modes with the same detector unit/assembly.

In a preferred embodiment, the operation of the dynamically-controllable light source and the detector unit/assembly is time-controlled such that different detection or imaging modalities are employed in a time-multiplexed manner, of which at least one modality involves multi-photon processes, wherein the modalities include one or more of two photon excited fluorescence, second harmonic generation, third harmonic generation and confocal microscopy.

Preferably, the dynamically-controllable light source comprises a first sub-light source, said first sub-light source being electrically controllable such as to generate controllable time-dependent intensity patterns of light having a first wavelength.

In addition, the dynamically-controllable light source may comprise a Raman-active medium suitable to cause a Raman scattering of light having said first wavelength, a second sub-light source capable of emitting light with a second wavelength, said second wavelength being longer than said first wavelength, and an optical fiber or waveguide, wherein said light emitted by said first and second sub-light sources traverses a length of said optical fiber or waveguide in a feed-forward configuration to facilitate a non-linear wavelength conversion step involving said Raman-active medium. Herein, at least one of the first and second sub-light sources may have a coherence length longer than 0.05 mm, preferably longer than 0.5 mm and most preferably longer than 2 mm.

Preferably, in the invention, the first sub-light source is electronically controllable such as to generate controllable time-dependent intensity patterns. Further, the light source comprises an optical fiber or wave guide in which the light emitted by the first and second sub-light sources traverses the length of said optical fiber in a feed-forward configuration to facilitate a non-linear wavelength conversion step involving the Raman-active medium. Herein, the "feed-forward configuration" can be a 1-4 pass feed-forward configuration. The "Feed-forward configuration" distinguishes the light source from a resonator-based light source. A feed-forward or "resonator-less" light source allows for flexible and fast electronic control of the intensity pattern.

Further, according to this aspect of the invention, at least one, preferably both of said first and second sub-light sources have a minimum coherence length. In particular, one or both of the first and second sub-light sources has a coherence length longer than 0.05 mm, preferably longer than 0.5 mm and most preferably longer than 2 mm.

The inventors have found out that surprisingly, if the first and/or second light sources have a sufficient coherence length, higher numbers of Raman shifts can be obtained while keeping the band width of the light signal below the width normally occurring due to spontaneous Raman emission in the Raman active medium. In fact, it is seen that consecutive Raman-shifted light signals can be obtained having a much narrower bandwidth than what would be expected from spontaneous Raman emission and which is shifted in frequency by multiples of the frequency difference between the first and second wavelength light. While a narrow bandwidth would be understandable for the first order Raman shifted light matching the second wavelength light due to the stimulated emission, for the higher order wavelength shifted light this is entirely unexpected, as there is no appropriate wavelength light source that could cause stimulated Raman scattering based on the first or higher order wavelength shifted light. Instead, for the "second or higher orders" of shifted light, it would appear that only vacuum fluctuations would be available for stimulating Raman emission, or in other words, a spontaneous Raman emission type process is expected to occur. Herein, the "order" of a shift shall indicate how many combined Raman processes are involved. For example, a third order shift would lead to a wavelength shift that corresponds to three times the frequency difference between the first and the second wavelength light. In the present disclosure, reference is made to "combined" Raman processes rather than "cascaded" Raman processes for reasons explained in more detail below.

Accordingly, it was surprisingly found that even for the "second order" shift a narrow Raman emission can be obtained that is much narrower than what would be expected from spontaneous Raman emission and that is shifted precisely by the frequency difference between the first and the second wavelength light. It thus appears that even for the generation of the second and the higher order wavelength shifts, the first wavelength light is involved in the combined Raman shift process. It is currently believed by the inventors that the underlying process is a four-wave-mixing type process which combines two Raman processes. This is why herein the term of "combined Raman processes" is used rather than cascaded processes, because the term "cascaded" relates to independent processes occurring one after the other. In a preferred embodiment, the wavelength converted light resulting from the wavelength conversion step has likewise a coherence length longer than 0.05 mm, preferably longer than 0.5 mm and most preferably longer than 2 mm.

In another embodiment, the coherent dynamically-controllable light source comprises
  a first sub-light source, said first sub-light source being a light source operating substantially in continuous wave mode,
  an electronically controllable modulator for modulating the light emitted from the first sub-light source such as to generate controllable time-dependent intensity patterns,
  a fiber amplifier for amplifying the modulated light generated by said first sub-light source and modulated by means of said modulator,
  a Raman active medium suitable to cause Raman scattering of light having said first wavelength and exhibiting a wavelength shift within a range of Stokes shifts,
  a second sub-light source capable of emitting light with a second wavelength, said second wavelength being longer than said first wavelength and differing from said first wavelength by a wavelength shift within said range of Stokes shifts, wherein said second sub-light source operates substantially in continuous wave mode, wherein light generated by said first sub-light source and modulated by said modulator, and light generated by said second sub-light source are fiber-coupled into said Raman active medium.

This design allows for a very flexible control of the output light pattern. In particular, the modulator may allow modulating the substantially continuous wave light from the first sub-light source with a modulation frequency of more than 100 kHz, preferably more than 500 kHz and most preferably more than 1 MHz. In particular, the modulator can be electronically controlled to configure the time delay between each two consecutive pulses with a mean repetition rate of 10 kHz or more, preferably 100 kHz or more, and most preferably 1 MHz or more.

Preferred embodiments of the light sources according to either one of the first or second aspects of the invention are discussed in the following.

In a preferred embodiment, the light source further comprises a modulator for modulating light generated by the first or second sub-light source.

Herein, the modulator may be one of
  an electro-optical modulator,
  an acoustic-optical modulator, or
  a swept Fabry-Pérot filter.

Among these modulators, an electro-optical modulator is particularly preferred because it allows generating almost arbitrary intensity patterns in a simple way, for example, under the control of a programmable function generator and/or a triggerable pulse generator. In particular, the modulator can be electronically controlled to generate one or more of:
  a CW light signal
  a periodic sinusoidal modulation or
  a light pulse pattern.

In a preferred embodiment, the pulse lengths of the light pulse pattern are at least 10 ps, preferably at least 20 ps and most preferably at least 30 ps. In addition or alternatively, the pulse length may be 50 ns or below, preferably 10 ns or below and most preferably 2.5 ns or below.

Preferably, at least one of the first and second sub-light sources is a laser light source, and in particular a semiconductor laser light source, preferably a semi-conductor laser diode.

The first sub-light source may have a wavelength in the range of 950 nm to 1200 nm, preferably in the range of 1000 to 1150 nm.

In a preferred embodiment, the first sub-light source has a wavelength of 1044 nm to 1084 nm, for optimum comparability with YAG laser optics.

In an alternative preferred embodiment, the wavelength of the first sub-light source may be in the range of 1010 to 1050 nm, for optimum amplification using Ytterbium as a gain medium.

In a yet further preferred embodiment, the wavelength of the first light source is between 950 nm and 1050 nm for enabling a maximum Raman shift.

Preferably, the wavelength of the second sub-light source is red-shifted compared to the wavelength of the first light source by 300 to 700 cm$^{-1}$.

In a further preferred embodiment, the first sub-light source may have a wavelength of 1450 to 1700 nm, preferably of 1480 to 1650 nm.

In a preferred embodiment at least one of the first and second sub-light sources has a spectral width narrower than 1 nm, preferably narrower than 0.1 nm.

In a preferred embodiment, the light source is operable with a duty cycle of less than 10%, preferably less than 1% and most preferably less than 0.1%. The instantaneous power may be more than 10 W, preferably more than 100 W, more preferably more than 300 W and most preferably more than 1 kW.

In a preferred embodiment, the light source comprises at least one optical amplifier. The optical amplifier may for example be used to amplify the light signal generated by the first sub-light source and modulated by the aforementioned modulator.

In a preferred embodiment, the at least one optical amplifier comprises a gain medium and a third sub-light source for pumping said gain medium. Herein, the gain medium is preferably a rare-earth doped optical fiber, wherein said rare-earth is preferably one or more of Ytterbium, Erbium, Thulium, Holmium and Praseodymium.

A number of this type of optical amplifiers can be arranged in series to provide consecutive amplification stages. Such amplifiers are also referred to as master oscillator power amplifiers (MOPAs) in the art.

In a particularly preferred embodiment, at least one of the optical amplifiers comprises a double-clad fiber having a core portion formed by a rare-earth doped fiber and a cladding layer for guiding pump light. Herein, the core portion fiber is preferably a single-mode fiber and the cladding layer is providing multi-mode pump light. In this embodiment, the core portion carries the signal that is to be amplified only, while the pump light is guided in the cladding layer. Accordingly, the entire light capacity of the fiber can be dedicated to the light signal that is to be amplified. This compares favorably with applications where both, the pump light and the light signal to be amplified are confined to the same fiber. Further, since the cladding layer allows guiding multi-mode pump light, the intensity of the pump light can be comparatively high, thereby leading to a high amplification gain.

Preferably, the pump light is fed into the cladding layer in a direction opposite to that of the light propagating in the core portion. This avoids that the amplified light signal is contaminated with pump light.

In a preferred embodiment, the light source comprises two or more optical amplifiers, wherein between two optical amplifiers, a filter, in particular a laser line filter, is provided for filtering an amplified stimulated emission background. In this way the signal-to-noise ratio can be efficiently increased. In a preferred embodiment, the Raman-active medium is formed by an optical fiber, in particular a silica fiber.

The number of combined Raman shifts will depend on the length of the fiber. Preferably, the fiber length is selected such as to allow for at least two consecutive Raman wavelength shifts.

In a preferred embodiment, the non-linear wavelength conversion step is carried out in an optical amplifier, and in particular in the last optical amplification stage of the light source. Preferably, the light signal, i.e. the signal generated by the second sub-light source is introduced into the optical amplifier prior to or during amplification in the amplifier where the wavelength conversion step takes place. Namely, as long as the intensity of the original light signal generated by the first sub-light source and pre-amplified by one or more of the aforementioned amplifiers (i.e. the "first light signal") is still low, the Raman gain is made negligible, such that bringing in the light signal as a Raman-seed signal does not have any significant influence on the light. Only when the first wavelength light receives a strong amplification, the broadband Raman gain is seeded by the narrow second wavelength light (second light signal) acting as the Raman seed. In total, this leads to a narrow line width at the shifted wavelength, where the other properties of the initial signal generated by the first sub-light source can largely be conserved. In particular, this allows avoiding a parasitic Raman background in the spectrum.

In one embodiment, the second sub-light source may be a tunable light source, which in turn allows choosing the wavelengths obtainable by the wavelength conversion. For this, for example, a grating based tunable laser or a Fabry-Pérot tunable laser can be used. While in case of the combined Raman shifts several frequencies of output light are usually generated, the selection of the suitable wavelengths can be made using suitable filters at the location of use of the light. In some embodiments, however, the selection of the appropriate wavelengths can be achieved using optical filters in the fiber setup.

In some embodiments, the electro-optical modulator has a switch voltage of <40 V, preferably <10 V and most preferably <5.6 V.

The fibers used in the light source may be polarization-conserving fibers. In particular, the fibers may be single-mode fibers of the group SMF28 or its equivalents or Hi1060 or its equivalents.

If a double cladding fiber is used for one of the optical amplifiers, the core diameter may be at least 3 µm, preferably at least 5 µm, and more preferably at least 6 µm. In addition or alternatively, the core diameter may be 18 µm or less, preferably 12 µm or less and more preferably 9 µm or less. In practice, the core diameter of the double cladding fiber may correspond to that of the single mode fibers used in the setup, for a better overlap of the modes.

In a preferred embodiment, the pulse length generated by a first sub-light source can be variably adjusted. In the preferred embodiment, the light source comprises one or more optical isolators. In a preferred embodiment, the first and second sub-light sources are synchronized with each other. Preferably, this synchronization is established electronically and in particular based on sharing common electrical signals or phase-locking electrical signals involved in the time control of the respective sub-light source.

In a preferred embodiment, the first sub-light source is capable of generating pulse patterns having pulses that are spaced in time with a time distance of less than 10 ns, preferably less than 2 ns and particularly preferably less than 1 ns. This can be used to suppress stimulated Brioullin scattering.

The invention further relates to a method for generating coherent narrow band light comprising the following steps:

generating light having a first wavelength using a first sub-light source, generating light having a second wavelength using a second sub-light source, said second wavelength being longer than said first wavelength, superposing said first and second wavelength light in an optical fiber or waveguide, thereby facilitating a non-linear wavelength conversion step involving a Raman-active medium, wherein at least one of said first and second sub-light sources has a coherence length longer than 0.05 mm, preferably longer than 0.5 mm and most preferably longer than 2 mm.

DESCRIPTION OF THE PREFERRED EMBODIMENTS

Figure 1:
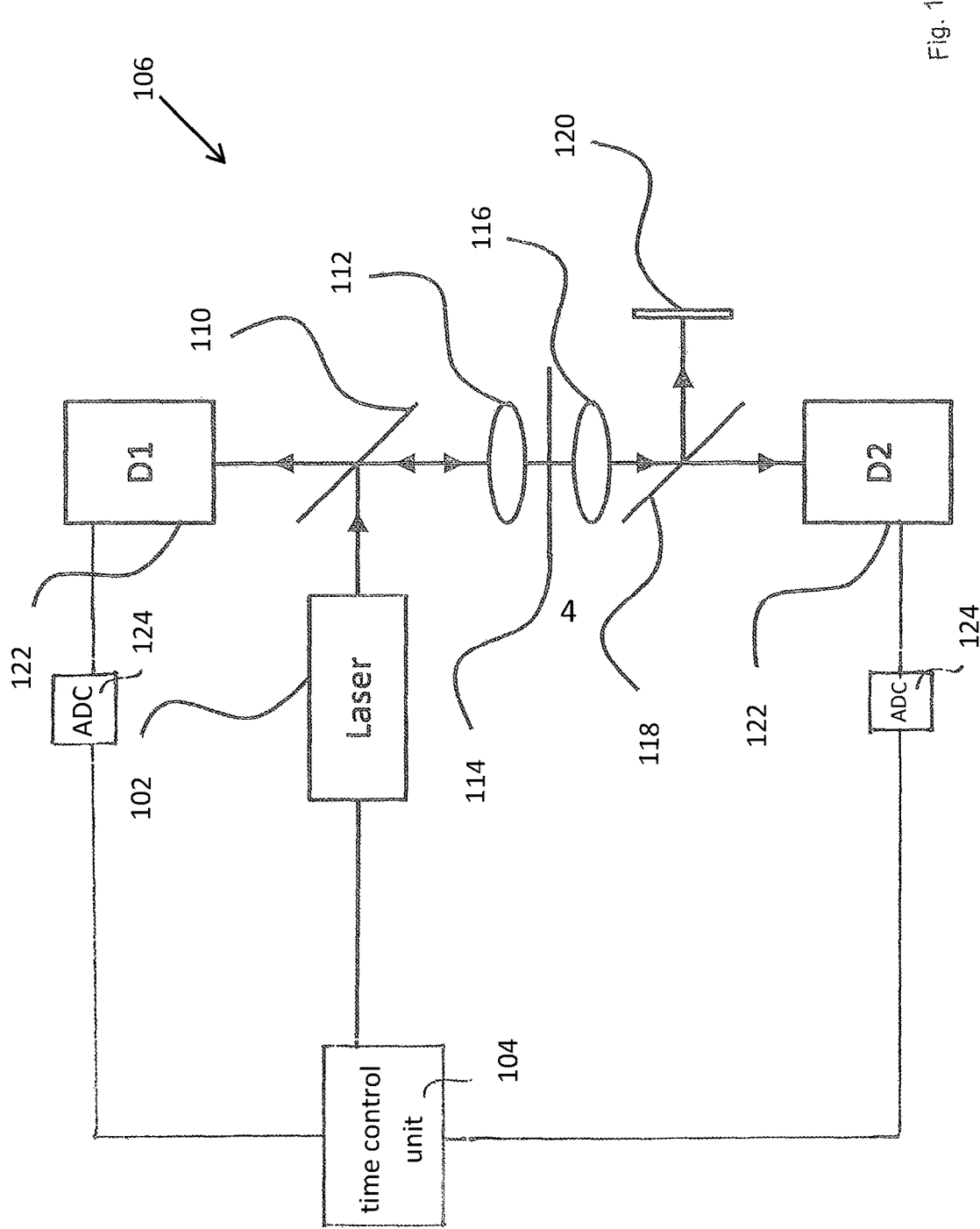
FIGS. 1 to 11 show different embodiments of the invention and measurement results obtained thereby.

For the purposes of promoting an understanding of the principles of the invention, reference will now be made to the preferred embodiments illustrated in the drawings and specific language will be used to describe the same. It will nevertheless be understood that no limitation of the scope of the invention is intended thereby, such alterations and further modifications in the illustrated device and method and such further applications of the principles of the invention as illustrated therein being contemplated therein as would normally occur now or in the future to one skilled in the art to which the invention relates.

In FIG. 1, a system 100 for inducing and detecting multi-photon processes, in particular multi-photo fluorescence and higher harmonic generation is schematically shown. As seen in FIG. 1, the system comprises a dynamically-controllable laser source 102 for generating high power light pulses. Under the time control of a time control unit 104, the time control unit 104 can for example be an arbitrary wavelength generator. Between the time control unit 104 and the laser 102 a pulse generator 106 is optionally present for generating short modulation pulses, for example for input to an electro optical modulator (not shown) employed in the dynamically-controllable laser source 102, which would only be triggered by the time control unit 104. Different designs of the laser source 102 will be described in more detail below.

In the embodiment of FIG. 1, the dynamically-controllable light source 102 serves to provide excitation light for a multi-photon process, such as multi-photon fluorescence. The excitation light beam 108 is deflected on a dichroic mirror 110, and focused by a lens 112 to a sample 114. While this is not apparent from FIG. 1, the largest part of the light path between the dynamically-controllable light source 102 and the sample 114 may be the light path between the laser 102 and the dichroic mirror 110, which in a preferred embodiment is formed by a single node fiber. After passing the sample 114, the excitation light beam passes a further lens 116 and is reflected off a further dichroic mirror 108 to a beam dump 120.

The light induced by the multi-photon process, for example multi-photon fluorescence, is generated at the sample location 114 and passed through the dichroic mirrors 110, 108 to respective photo detectors 122.

In the embodiment of FIG. 1 the photo detectors are connected with analog/digital converters 124 for digitizing the received electric signals. The analog-digital converters (ADC) 124 can be commercially available as boards or cards for a personal computer. As is seen in FIG. 1, the ADCs 124 are connected with a time control unit 104, allowing for a synchronization or a time correlation of the operation of the dynamically-controllable light source 102 and the detection by detectors 122. This way, time-resolved measurements with great flexibility become possible.

As mentioned before, the synchronization or time correlation can be obtained for example by using a common arbitrary waveform generator as the time control unit 104 or as part thereof, having several channels, of which one or more is used for control of the laser 102 and one or more is used for the control of the detectors 122 or the respective ADCs 124. If necessary, the channels can be synchronized using phase-locked loops or the like.

Note that the ADCs 124 may operate very rapidly, allowing for time-resolved measurements. In fact, the system 100 shown in FIG. 1 can even be used for fluorescence lifetime imaging, as the dynamically-controllable light source 102 can generate light pulses in the picosecond regime and the time resolution of the ADCs 124 is sufficient for time-resolved measurement of the lifetime.

Further, the time control of the detector 122 allows for making a time-gated detection such as to suppress background signals when no signal is expected. Due to the very flexible operation of both the dynamically-controllable laser 102 and the detectors 122, the multi-photon detection can also be used for cytometry. Herein, the multi-photon detection can help to identify cells and to classify them into the respective types. The timing of the excitation pulses, and in particular the repetition rate, as well as the excitation wavelength and the pulse patterns can be freely adjusted and optimized to the object under examination.

As will be explained in detail below, the dynamically-controllable light source 102 can operate at different excitation wavelengths. This is particularly useful for multi-photon interactions, because different absorption bands can be specifically addressed. Further, the dynamically-controllable light source 102 may operate in the near infrared light, which enables higher penetration depths as compared for example if Ti:Sa lasers are used.

Finally, the system 100 of FIG. 1 comprising the dynamically-controllable light source 102 is ideally suited for incorporating different imaging modalities in a single system. Due to the time control provided by the system, different imaging modalities can be used in a time multiplex approach, allowing for the same laser 102 and the same detector 122 to be used for different imaging modalities in different time slots. A generalization of the system 100 is shown at reference sign 200 in FIG. 2. The system 200 of FIG. 2 comprises several lasers 202 and several detectors 204. The system 200 further includes a sample at a sample site 206 that can be sequentially, but possibly also simultaneously, irradiated with light from different lasers 202, to thereby generate signals.

At least one of these signals is generated by or indicative of multi-photon processes at the sample 206, but other signals may be generated based on other imaging modalities, for example Raman Spectroscopy, confocal microscopy or the like. The detectors 204 are connected with a data acquisition unit 208 under the control of a time control unit 210.

Under the time control of unit 210, different lasers 202 and different detectors 204 can be operated in a time-multiplexed fashion, thereby allowing for a great flexibility of integrated different imaging modalities, but also using the same components for different imaging modalities in different time slots.

Figure 3:
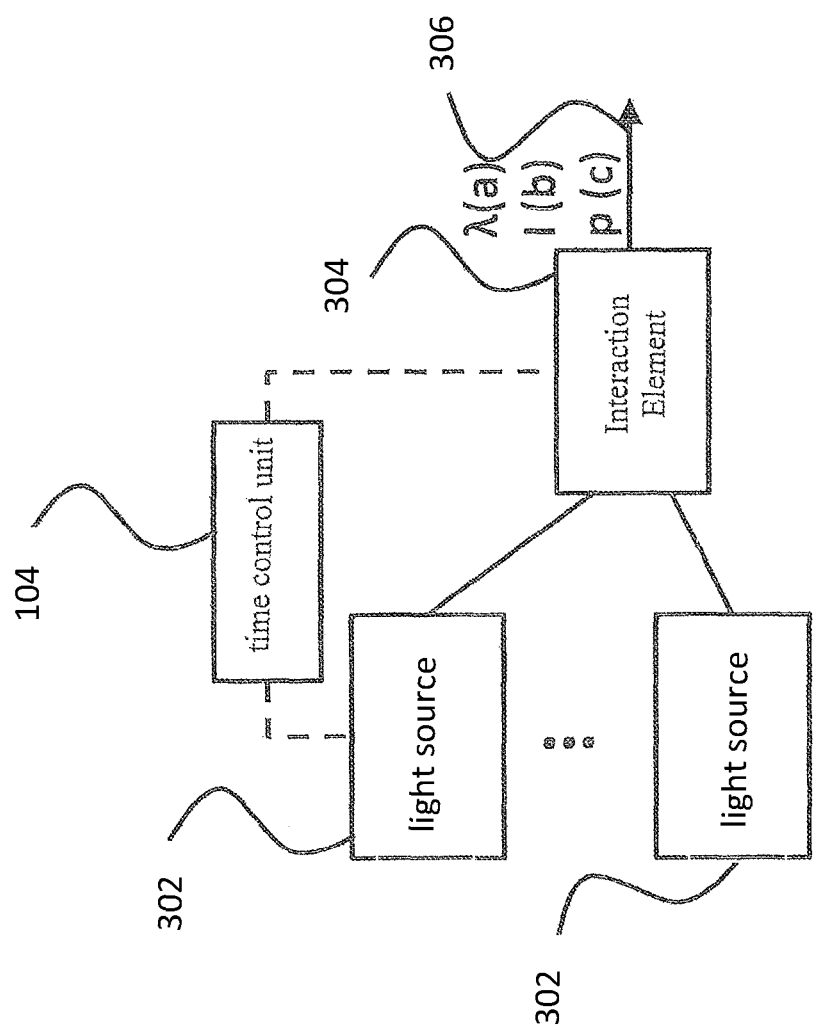

With reference to FIG. 3, a general structure of the dynamically-controllable light source 102 is shown. As is shown in FIG. 3, at least one, preferably two, particularly preferably three or more light sources 302 are provided, which are each controllable by a control element 104. The light emitted by the one or more light sources 302 is combined in an interaction element 304. The interaction in the interaction element may occur in different ways, such that the light 306 exiting the same has one or more specific wavelengths λ(a) with intensities I(b) and polarizations p(c). The parameters a, b and c can be adjusted by the control element 104 in various ways, for example by switching on/off light sources 302, changing pump powers, applying heating or cooling, controlling a filter element, mechanical adjustment of parts of the light source, e.g. by applying stress/strain on a fiber or the like, or by the actual implementation of the light sources 302 with regard to wavelength, power, spectral width and the interaction element, such as gain medium, interaction effect, nonlinear materials and the like. The active control by the control unit 104 allows for freely-adjustable modulation patterns and a synchronisation to other components.

Figure 4:
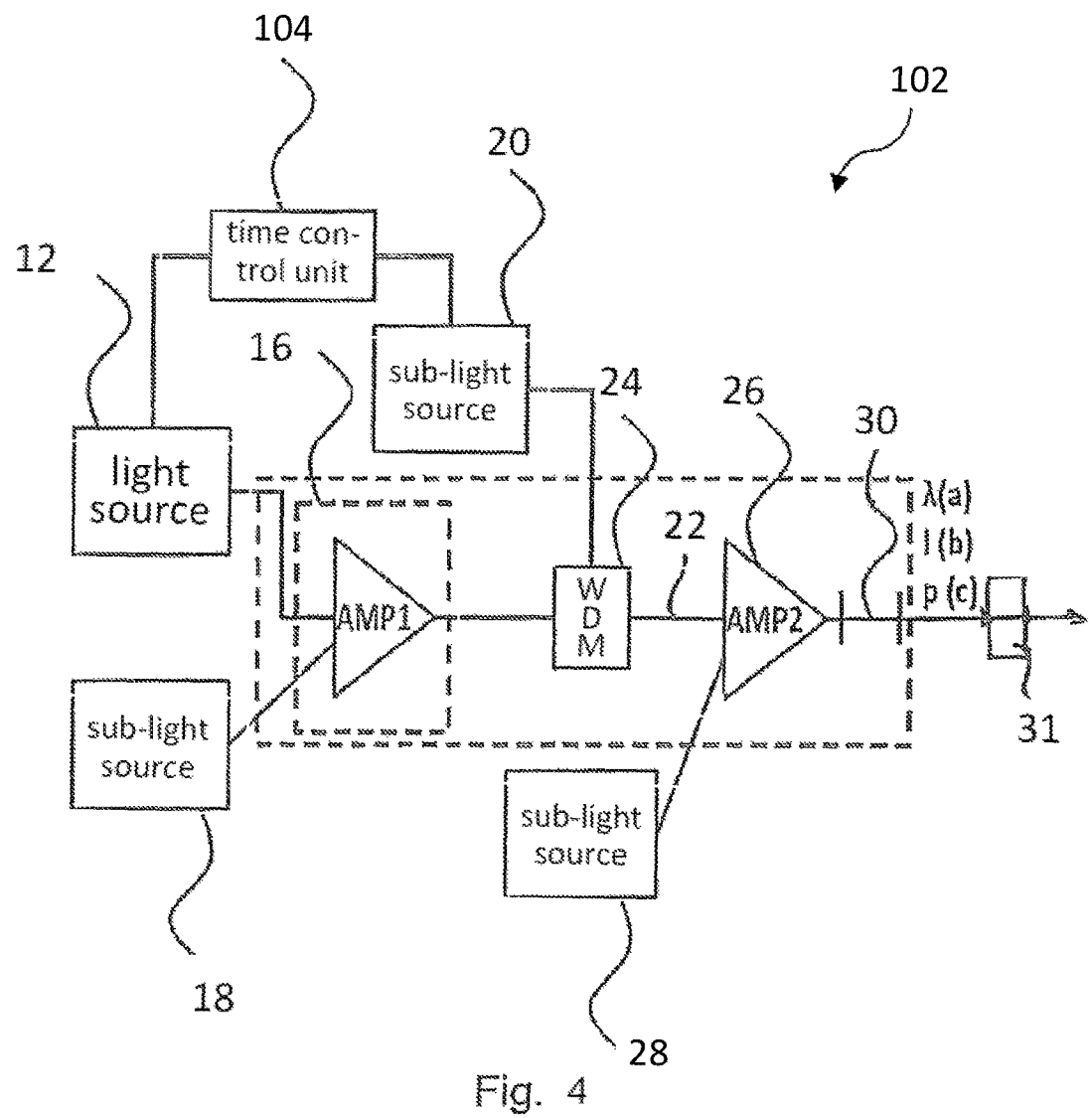

A specific implementation of the general light source 102 of FIG. 3 is shown in FIG. 4. In FIG. 4, a narrowband laser light source 12 resembling a first sub-light source generates an initial light signal, under the control of an electronic control unit 104. More precisely, the control unit 104 controls a suitable modulator (not shown) such as to arbitrarily modulate the amplitude and/or phase of the first sub-light source 12.

The light of the light source 12 may be modulated to the desired form. The light source 12 is preferably a semiconductor-based laser diode in the near infrared and most preferably in the spectral region of a fiber-based amplifier material like ytterbium, thulium, and erbium. An optical fiber Bragg-grating can be included to achieve a narrowband spectrum. It is also possible to let the first sub-light source 12 be a wavelength tunable light source. In particular, the first sub-light source 12 could be a rapidly tunable light source or swept light source, such as an FDML laser. The output of the first light source 12 is modulated under the control of the electronic control unit 104. For the modulation purposes, preferably an electro-optic modulator (EOM) is used. However, also an acoustic-optic modulator, preferably together with a swept Fabry-Pérot filter can be used. An EOM, for example, allows to create freely-adjustable modulations at high speeds. A preferred modulation would be a pulse pattern with successive pulses with pulse lengths shorter than 10 ns and longer than 10 ps with freely-configured timings between two pulses. The average repetition rates may be greater than 10 KHz, preferably greater than 100 KHz and most preferably greater than 1 MHz. The modulation component is preferably electronically controllable.

The modulated light signal of the first sub-light source 12 is then optionally amplified in an amplifier 16 having a gain medium that is pumped by a third sub-light source 18. While only one amplifier 16 is shown in FIG. 1, a plurality of amplifiers 16 can be arranged in series to thereby amplify the modulated output signal of the first sub-light source 12. The amplifier 16 resembles a master oscillator power amplifier configuration per se known from the literature. However, in the embodiment of FIG. 4, the problem of suppressing the amplified stimulated emission (ASE) underground is preferably solved in a way different from prior art. To filter the unwanted ASE underground, it is possible to introduce a free space filter configuration with narrow bandwidth optical filters at the desired wavelength. If the first sub-light source 12 is tunable, then it is possible to introduce a free space filter configuration with narrow bandwidth optical filters at the desired wavelength. For a tunable first sub-light source 12, it is also possible to build a tunable ASE filter by using a grating filter and tilt the grating for a different wavelength. Another possible filter configuration consists of an optical fiber circulator and a fiber Bragg-grating with peak reflection at the desired operational wavelength. The total output power of the amplifier 16 is preferably chosen in such a way that unwanted effects like stimulated Raman scattering or stimulated Brouillon scattering are circumvented.

With further reference to FIG. 4, the modulated and amplified output signal can optionally be shifted in wavelength using stimulated Raman emission. For this, a second sub-light source 20 generates a Raman shift seed-signal that is also fed into a Raman active medium, such as an optical fiber 22, 30. For this purpose, in the example of FIG. 4 a wavelength division multiplexer 24 is used. The Raman shift seed-signal generated by the second sub-light source 20 differs from the wavelength of the initial light signal generated by the first sub-light source 12 by a Stokes band of a Raman active medium, i.e. of the fiber 22, 30. The purpose of the Raman shift seed-signal is to induce stimulated Raman emission in a portion of the fiber 22, 30 to thereby generate a Raman-shifted output signal. For example, if the fiber 22 is a silica fiber of the type often used in telecommunication applications, a very intense signal can act as a pump source for a spontaneous Raman effect in the fiber 22. The strong narrow band pump signal would then usually be shifted towards a broad spectrum having a maximum intensity shift by 13 to 15 THz with respect to the pump signal. Using the Raman shift seed-signal generated by the second sub-light source 20, however, a stimulated emission is caused, and the broad spectrum known from the spontaneous Raman effect will be reduced to a narrow peak having the spectral properties of the Raman seed-signal.

The Raman-seed signal generated by the second sub-light source 20 may optionally also be wavelength tunable to adjust the whole bandwidth of the Raman gain. The Raman-seed is injected into the beam delivery fiber with an appropriate device, such as a wavelength division multiplexer (WDM) (not shown). It would also be possible to achieve the coupling in a free space configuration with dichroic mirrors. The Raman-seed signal can be operated in the CW mode, a modulation is however also possible. Using polarization controllers (not shown) provides the possibility to adjust the polarization to that of the light of the first sub-light source. It is also possible to construct the entire light source 102 from polarization maintaining fibers. Note that by fast switching on and off the second sub-light source 20 and hence the Raman-seed signal, it is possible to rapidly switch the excitation wavelength. This can in fact achieve switching times on the order of magnitude of the pulse repetition rate.

Note that stimulated Raman scattering in an optical fiber only occurs at a significant amount when high powers are applied. For this, a second amplifier 26 may optionally be provided which likewise comprises a gain medium and is pumped by a forth sub-light source 28. While the fibers 22, 30 and the second amplifier 26 are shown as separate objects in the schematic view of FIG. 1, amplification and Raman shift may at least in part take place in one and the same fiber. The inventors have found out that it is advantageous to actually feed in the Raman shift seed-signal prior to the last amplification stage 26. Namely, as long as the intensity of the original light signal as generated by the first sub-light source 12 and preamplified by the amplifier 16 is still low, the Raman gain is negligible, such that bringing in the seed-signal does not have any significant impact on the light. Only if the original light receives a strong amplification in the second amplifier 26, the broad band Raman gain will be seeded by the narrow Raman seed. In total this leads to a narrow line width at the shifted wavelength, wherein the pulse properties of the initial signal generated by the first sub-light source 12 can largely be conserved. In particular, this allows avoiding a parasitic Raman background in the spectrum.

The second amplifier 26 may be of a similar construction as the first amplifier 16. In an alternative embodiment, the amplification can also be accomplished using double-clad fibers, where the signal propagates in a single-mode core and the pumping is done in a multi-mode cladding. This way, higher pump powers can be employed. The core diameter is preferably between 3-20 µm, especially preferred 10 µm, as in standard tele-communication single-mode fibers. An active ytterbium double-clad fiber may be pumped by high-power multimode light sources as the fourth light source, which are coupled to the double-clad fiber by beam combiners. This way, it is possible to pump in counter-propagating direction so as to avoid any pump light leaking into the signal light direction.

With further reference to FIG. 4, downstream of the second amplifier 26, an optical fiber 30 is shown which may act as the Raman active medium for further intended wavelength shifts. Based on the length of the optical fiber 30, the Raman shift can be repeated in the sense that two or more Raman shifts may occur in sequence, thereby allowing for another one or even more wavelength shifts. The optical fiber 30 can also be split into different fibers of different lengths to generate outputs with different wavelength shifts due to a different number of consecutive Raman shifts.

In fact, the inventors noticed that in the fiber 30, the Raman shifts are not simply "repeated" in the sense of a cascaded Raman scattering process where the individual Raman processes are unrelated to each other. Instead, provided that the coherence lengths of the first and/or second light sources 12, 20 are sufficiently long, it is seen that the first sub-light source light also plays a role in the generation of "second order" Raman shifted light, i.e. the light that is shifted towards longer wavelengths as compared to the second wavelength by a wavelength corresponding to the frequency difference of the first and second light sources. This is evidenced by the fact that the frequency shift between the second order Raman shifted light and the first order Raman shifted light matches precisely the frequency difference between the first and second light sources, and that the second order Raman shifted light has a bandwidth that is much narrower than the ordinary bandwidth expected from spontaneous Raman emission. Accordingly, by providing for sufficient coherence length in the first and/or second light sources 12, 20 this effect can be used to generate narrowband shifted output light that is considerably narrower than the inherent Stokes band of a fiber that would in fact lead to frequency shifts in a rather broad range of 13 to 15 THz.

Through electrically-adjustable light power or switching of the Raman-seed, one can control the cascaded Raman effect which leads to different, e.g. higher or lower wavelengths. Thereby, the timing and spectral characteristics of the initial light signal is maintained throughout the shifted light. The aforementioned light shift accomplished by spontaneous Raman scattering is reduced to a narrow band light upon stimulating Raman scattering, effectively maintaining the spectral characteristic of the Raman-seed signal provided by the second sub-light source 20, if it is switched on. If the power levels and interaction length, i.e. fiber length, are sufficient, this narrow-band Raman shift can be cascaded to further wavelengths. As mentioned before, with this cascaded shift it is possible to create a multitude of spectral peaks, each being equidistant and having comparable power levels.

The intensity of a single peak is adjusted through the applied power and/or the interaction fiber length. Nevertheless, it is also possible to achieve comparable power levels of many different spectral peaks. Through electronic switching it is thus possible to switch instantaneously between the wavelengths. The switching can occur preferably in less than 1 s, in less than 1 ms, in less than 1 µs but most preferably in less than 10 ns, making the switching between wavelengths much faster than commonly-used optical parametric amplifiers.

Figure 2:
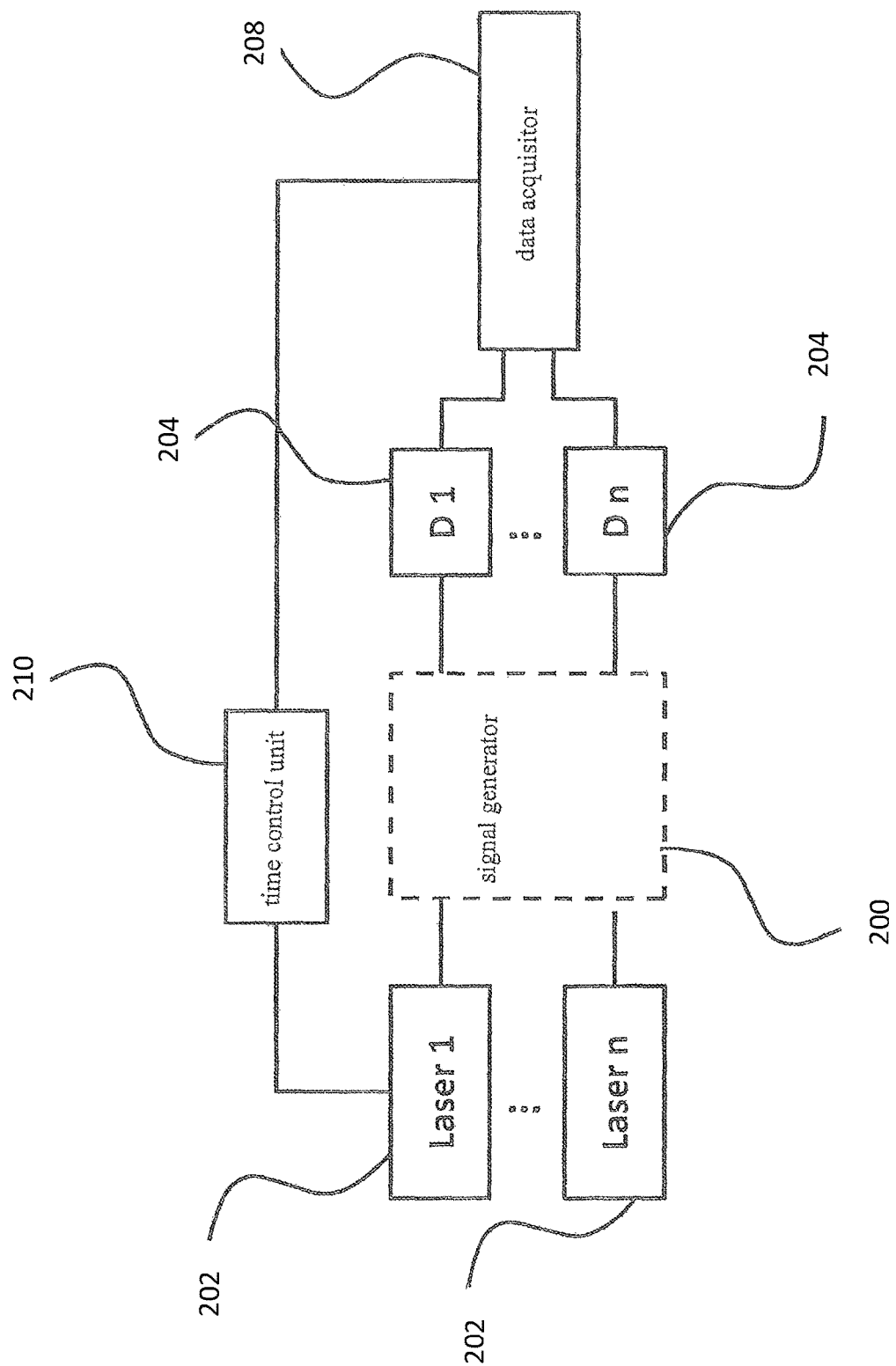

Further, while not shown in FIG. 2, another applicable wavelength conversion process can be driven by four-wave mixing, in particular generated by means of crystals (e.g. BWO) or in a fiber-based fashion, for example by using modulation instability.

As is further shown in FIG. 4, at the end of the fiber 30, a non-linear optical element 31 for frequency doubling can optionally be provided. Suitable non-linear elements are non-linear crystals or periodically-poled materials, such as PPKTP, PPLL, or PPLT. This way, the multi-photon interaction in the object under examination can be excited by a mixture of frequency-doubled light and non-modified wavelengths. This leads to a broad range of possible multi-photon interaction wavelengths. For example, the combination of 1550 nm light with frequency-doubled light of 1064 nm light source at 532 nm can lead to an effective excitation at 396 nm.

The second sub-light source 20 may be a tunable laser light source, for example a grating based tunable light source or a Fabry-Pérot tunable laser. One or all of the sub-light sources 12, 18, 20, 28 may have a polarization analyzer or other polarization control means. This is particularly important for the second sub-light source 20, because the Raman gain strongly depends on the polarization of pump and Stokes light. It is maximal for parallel and minimal for orthogonal polarization. Since there are birefringence fracturations in the fiber, the polarization of the Stokes and pump light will change for each wavelength differently during propagation in the fiber. This will lead to different gains if different stress or strain is applied to the fiber or if temperature changes are present, as these effects have an impact on the birefringence of the fiber. To be able to optimize the polarization in terms of the above mentioned impacts, a polarization analyzer or polarization controller is preferably used in the generation of the Raman shift seed light.

The wavelength of the first sub-light source 12 is preferably between 1044 and 1084 nm, preferably between 1054 and 1074 nm, because this allows for a compatibility with most YAG laser optics. In an alternative embodiment, the output wavelength of the first sub-light source 12 is between 1010 and 1050 nm, more preferably between 1020 and 1040 nm, because this allows for a maximum amplification using Ytterbium as the gain medium, which is a preferred material for this purpose. In yet an alternative embodiment, the wavelength of the first sub-light source 12 is in the range of 950 to 1050 nm, preferably 980 to 1020 nm, to allow for a maximum Raman shift.

Preferably, the wavelength of the Raman shift seed signal is redshifted as compared to the wavelength of the first sub-light source 12 by 300 to 700 $cm^{-1}$, preferably by 400 to 600 $cm^{-1}$.

Figure 5:
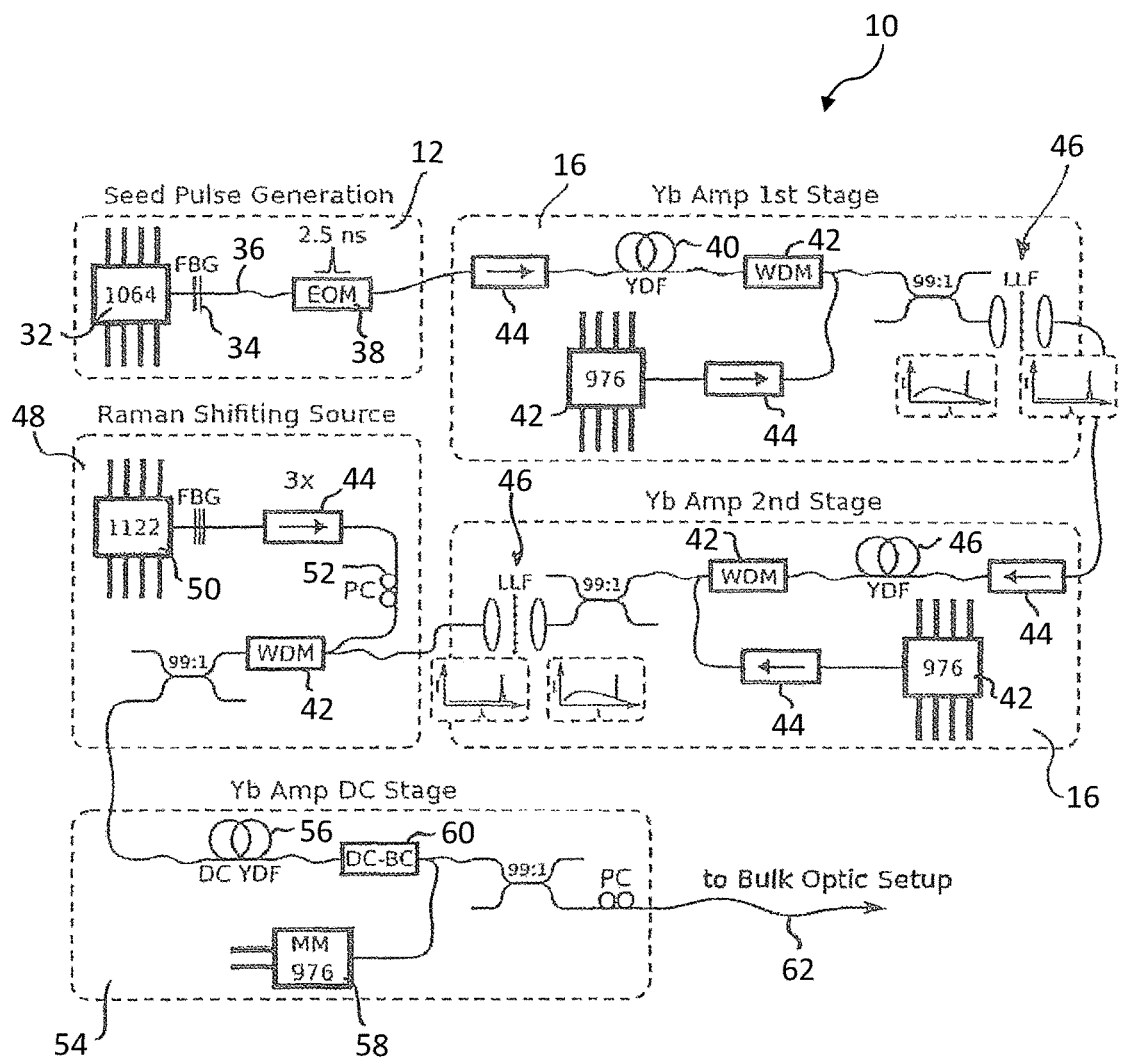

With reference to FIG. 5, a specific embodiment of the light source 102 according to FIG. 1 is shown. Corresponding components are designated with identical reference signs.

As shown in FIG. 5, a first sub-light source 12 is provided for generating a seed light pulse. The first sub-light source 12 comprises a 1064 nm laser diode 32 with a fiber Bragg grating 34. The laser diode 32 is connected via a polarization maintaining fiber 36 to an electro optical modulator 38 which modulates the light signal from the laser diode 32 to generate pulses with a duration of 2.5 ns at desired timing, under control of a control unit like the control unit 14 of FIG. 1, which is not shown in FIG. 2. Actually, the electro optical modulator 38 would allow for shorter light pulses, as short as 100 ps only if desired.

Downstream of the first sub-light source 12, a first amplification stage 16 is provided. The first amplification stage 16 comprises an Ytterbium doped fiber 40 as a gain material which is pumped by a 976 nm laser diode 42. The pump light is coupled into the Ytterbium doped fiber 40 by means of a wave division multiplexer (WDM) 42. In the optical fibers, isolators 44 are further provided. The length of the Ytterbium doped optical fiber 40 is chosen to yield a good compromise between gain and amplified stimulated emission (ASE). A preferable length of the Ytterbium doped fiber 40 is between 1.5 and 2.5 meters.

The thus amplified light signal is fed through a laser line filter 46 into a second amplification stage 16 which is generally the same as the first amplification stage 16 and therefore does not need to be described again.

The laser line filter 46 serves to filter the ASE background, as is apparent from the illustrative boxes shown in FIG. 2. Instead of laser line filters, other filter designs can be used.

A Raman shifting source 48 is provided for generating a Raman shift seed signal. The Raman shifting source corresponds to the second sub-light source 20 in FIG. 1. The Raman shifting source 48 comprises a 1122 nm laser diode 50 which may be selectively turned on or off under control of a control unit (not shown), depending on whether a Raman shift of the output light is intended or not. Light from the 1122 nm laser diode 50 is fed through a polarization controller 52 allowing adjusting the polarization of the Raman shift seed signal such as to cause an optimum stimulated Raman emission. The polarization adjusted light from the 1122 nm light source 50 is coupled into the 1064 nm light pulse signal that was shaped by the electro optical modulator 38 and amplified in the two amplification stages 16 via another WDM 42.

Both, the 1122 nm Raman shift seed signal and the pre-amplified 1064 nm pulse are fed into a final amplification stage 54 which is also referred to as a double clad (DC) amplification stage schematically shown in FIG. 2. A double clad fiber usually consists of three layers of material, namely a core, a first cladding and a second cladding. With a decreasing refractive index from core to second cladding, light can be guided in the core and in the first cladding, respectively. The final amplification stage 54 comprises a double cladding fiber 56 having a single-mode Ytterbium doped core and a first cladding, to which 976 nm pump light generated by a 976 nm multimode pump source 58 is fed via a double clad-beam combiner 60.

Since multi-mode pump light is fed into the first cladding of the double cladding fiber 56, a very strong amplification can be generated. Namely, using a multimode diode 58 higher intensities can be achieved as compared to a single mode diode. Also, while in the first and second amplification stages 16 the single-mode Ytterbium doped fibers 40 need to carry both, the signal as well as the pump light, in the double clad fiber 56 of the final amplification stage 54, the Ytterbium doped core fiber is reserved for the signal only, such that the full capacity thereof can be used for the signal. As seen in FIG. 2, the multimode pump light is directed in opposite direction to the propagation direction of the signal within the core of the double clad fiber 56 such that the pump light will not contaminate the amplified 1064 nm light.

When the laser diode 50 of the Raman shifting source 48 is turned off, the final amplification stage 54 simply amplifies the 1064 nm pulse. However, if the Raman shifting source 50 is turned on, the light of the Raman shifting source 48 acts as a stimulated Raman emission seed signal within a fiber 62 leading to a bulk optic setup or some sample location or the like (not shown in FIG. 2), where the light generated by the light source 10 is to be employed.

This light source 10 as shown in FIG. 5 is ideally suited for many applications, because it allows
  generating short light pulses at precisely electronically configurable, programmable timings,
  generating very high peak powers of several kilowatts and for optional frequency shifts while maintaining a narrow band width.

As was explained above, the number of repeated Raman shifts arising will depend on the length of the fiber 62. Accordingly, the desired wavelength shift can be controlled by the length of the fiber 62. In some embodiments, fibers 62 with different lengths can be attached, giving rise to the desired number of repeated Raman shifts, or, in other words, the desired output wavelength. It is also possible to permanently attach a short fiber 62 (for 1122 nm light) and a longer fiber 62 (for 1185 nm light) using a suitable coupler, and yet longer fibers 62 for even longer wavelengths.

In one embodiment, the amplification and Raman shift occur simultaneously in the same optical fiber. In one embodiment, a tunable light source is used for generating the Raman shift seed signal, which in turn allows choosing the wavelength obtainable by the combined stimulated Raman shifts. For this, for example, a grating based tunable laser or a Fabry-Pérot tunable laser can be used. While in case of the repeated Raman shift several frequencies of output light are usually generated, the selection of these suitable wavelengths can be chosen using suitable filters at the location of use of the output light. In some embodiments, the selection of the appropriate wavelengths can be achieved using a fiber Bragg grating which is connected via a circulator. It is, however, also possible to select the wavelengths using optical filters in the fiber setup.

In some embodiments, the modulator 38 is an electro optical modulator having a switch voltage of <40 Volt, preferably <10 Volt and most preferably <5.6 Volt.

In some embodiments, the seed signal is modulated, by means of the EOM 38, with a frequency of more than 200 MHz, preferably more than 500 MHz, more preferably more than 1 GHz, more than 2.5 GHz or more than 10 GHz, with regard to either one of amplitude or phase.

Moreover, some of the fibers used in the light source 10 may be polarization conserving fibers. In particular, the fibers may be single-mode fibers of the group SMF28 or its equivalents or Hi1060 or its equivalents.

In an alternative embodiment, the first sub-light source 12, i.e. the "seed light source", can be made tunable. In particular, the first sub-light source 12 could be a rapidly tunable light source or swept light source, such as an FDML laser that can be used together with a modulator such as the EOM 38 shown in FIG. 2. However, other tunable light sources can likewise be used for the seed pulse generation.

Further, instead of the laser line filters 46 shown in FIG. 5, which are used for suppressing the spectral background caused by the rare earth doped fiber amplifiers, a combination of an optical circulator and a fiber Bragg grating may be used, such that a completely fiber-based setup can be achieved. In addition or alternatively, narrowband wavelength division multiplexers, fiber Fabry-Pérot filters or fiber-based spectral filter elements can be employed.

Figure 6:
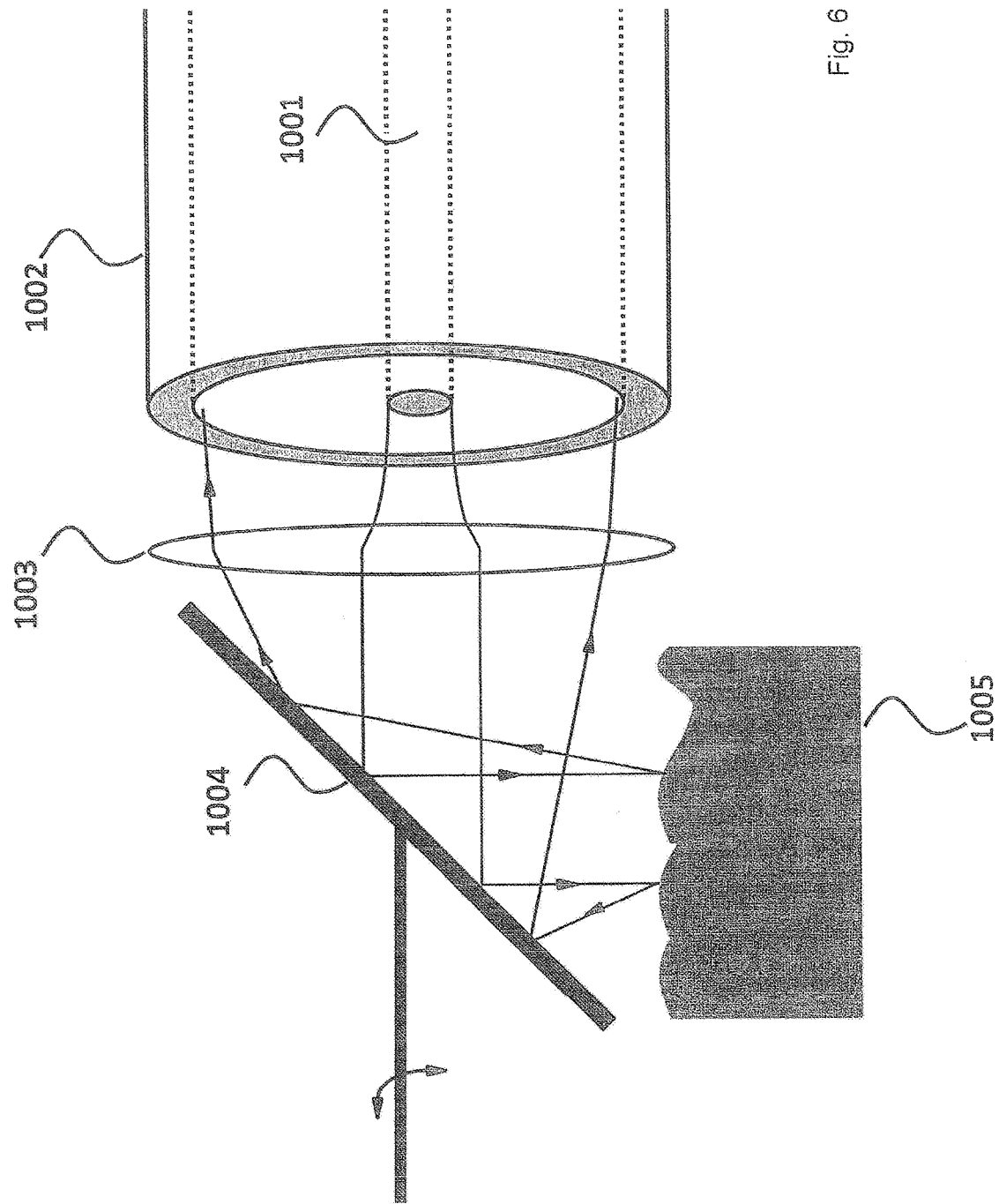

FIG. 6 shows how the system and the invention can be employed in an endoscopic application. As shown in FIG. 6, the excitation light is fed through a single-mode core 1001 of a double-clad fiber 1002. Through a rotatable mirror 1004 and optimally also through a lens 1003, the excitation light is delivered and/or focused on an object 1005. The rotations of the mirror are e.g. driven by a motor or are magnetically induced. Instead of a double-cladding fiber, it is also possible to use a fiber bundle. Furthermore, a fiber bundle endoscope with endscanning can be used, i.e. where the end of the fiber is scanned with regard to a sample. Instead of using a rotating mirror, it is also possible to use a fixed mirror or a prism or other deflection means which can be coaxially rotated.

Figure 7:
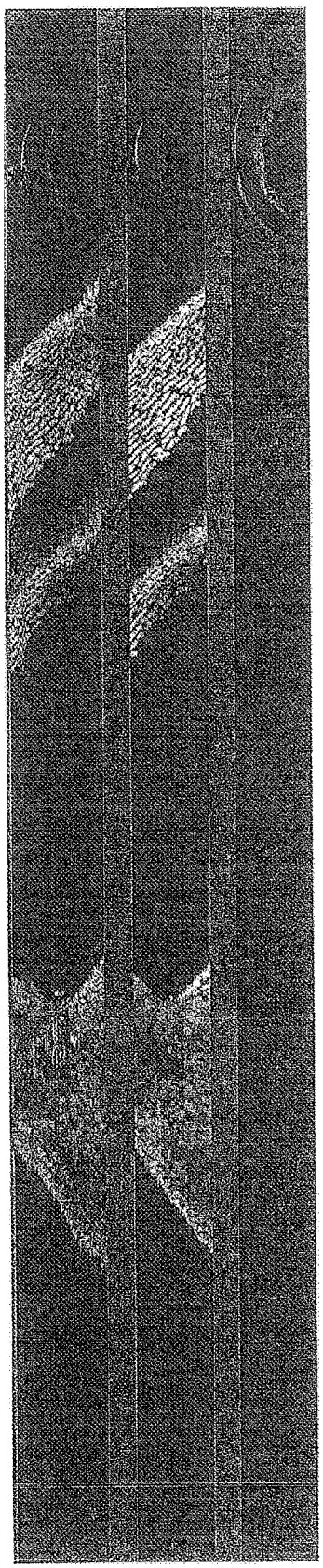

With reference to FIGS. 7 to 11, results of two-photon-fluorescence and higher harmonic generation measurements employing a system according to an embodiment of the invention are shown. In FIG. 7, the upper image shows both, a second harmonic generation (SHG) and a two-photon-excitation fluorescence (TPEF) image. The image in the middle shows only the TPEF image, and the bottom image shows only the SHG image.

Figure 8:
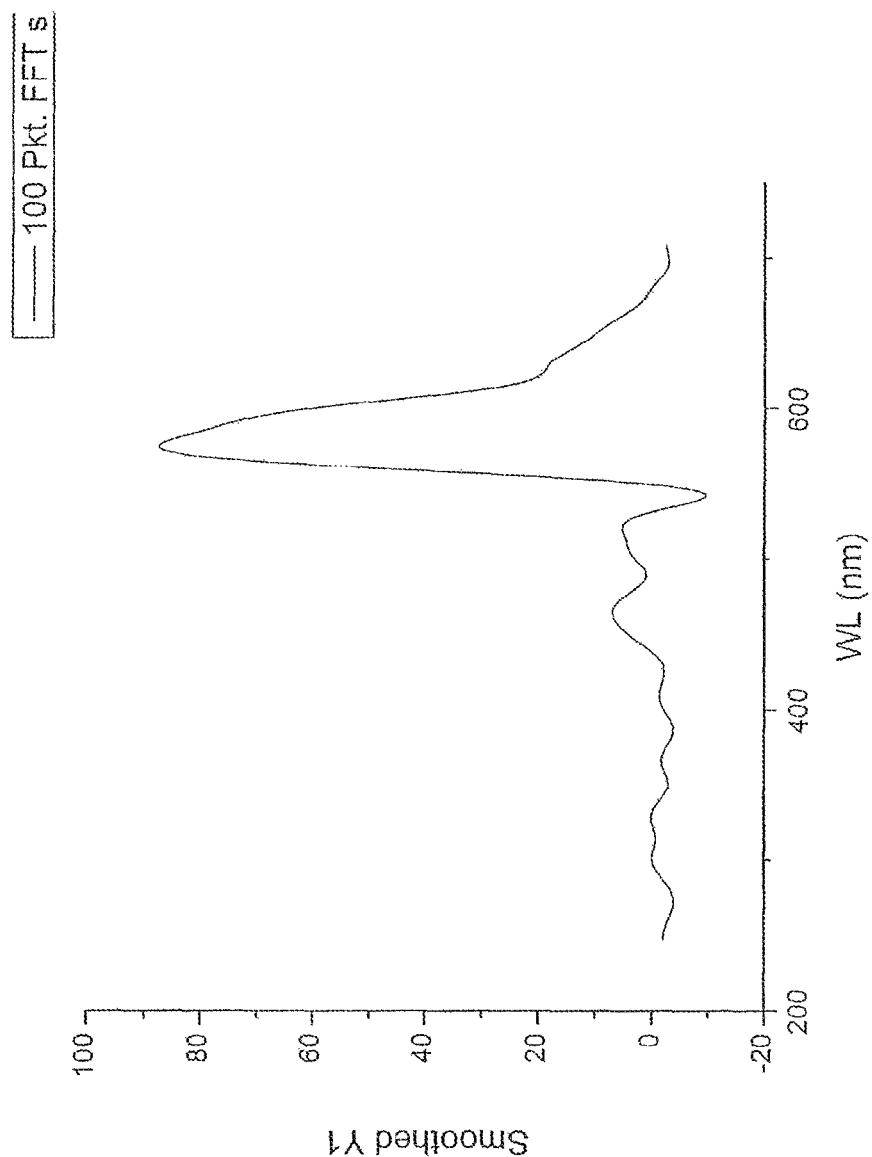

FIG. 8 shows the spectrum of the fluorescence of the dye Rhodamin 6G. The dye was excited through multi-photon interaction of intense 1064 nm light, and the fluorescence was recorded with a spectrometer.

Figure 9:
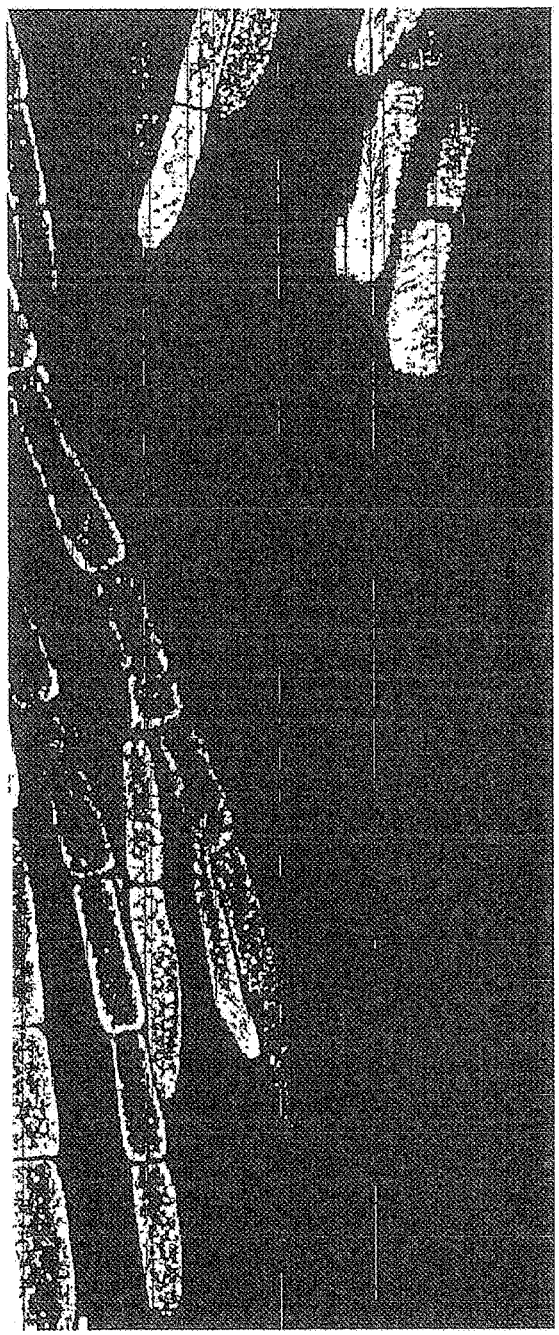

FIG. 9 shows a microscopic image of the multi-photon interaction signals of chlorophyll in algae. The bright areas resemble the chlorophyll.

Figure 10:
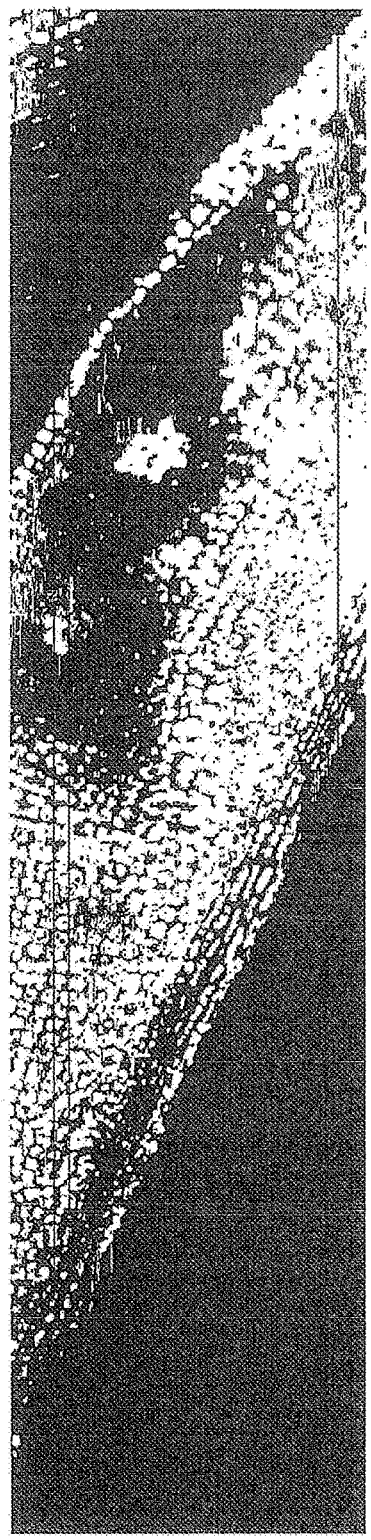

FIG. 10 shows a microscopy image of the multi-photon interaction signals of chlorophyll in moss. The bright areas resemble the chlorophyll. The image is 2 mm wide.

Figure 11:
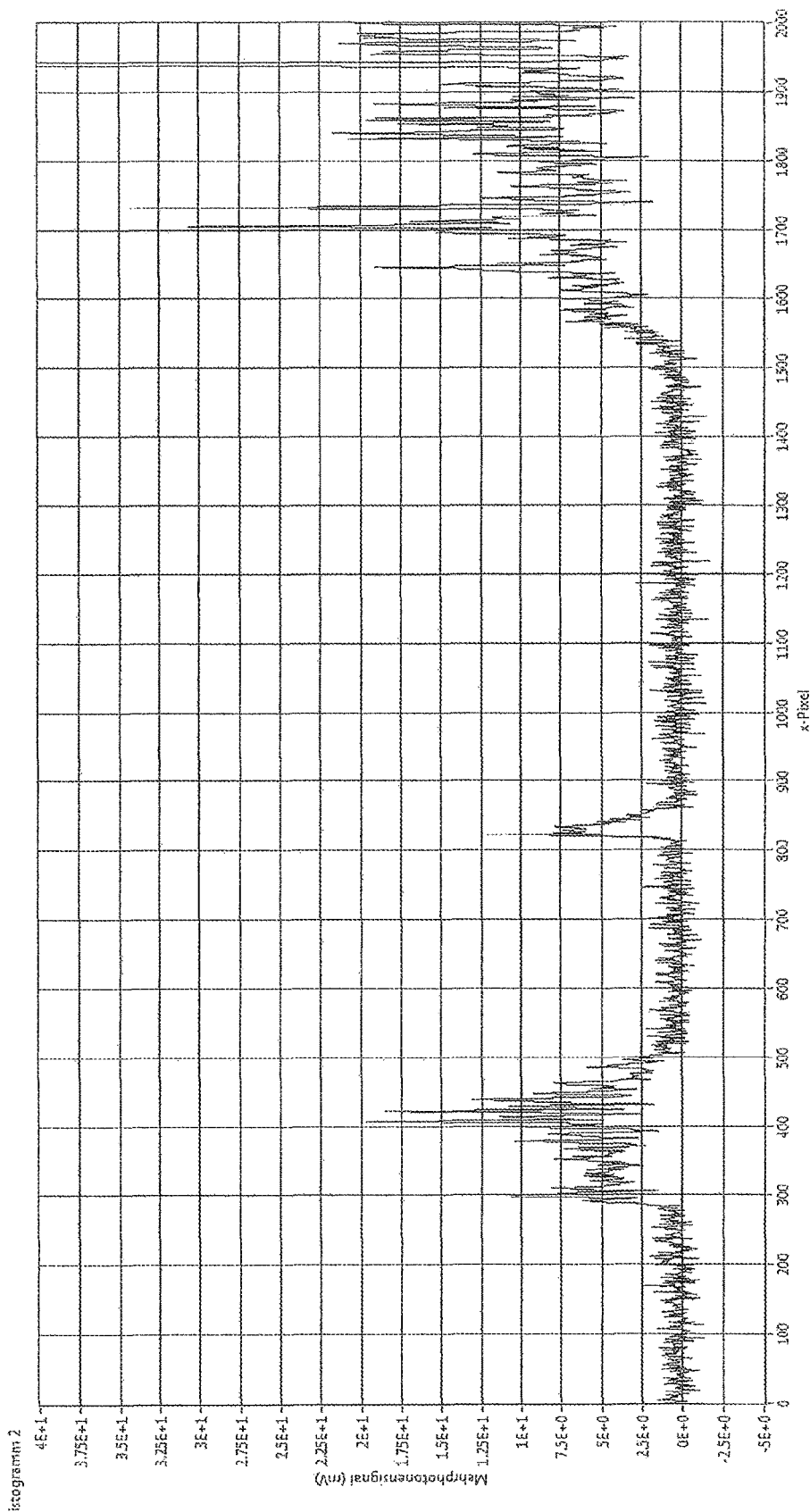

Finally, FIG. 11 shows a histogram of one line of the microscopy image of FIG. 10. The multi-photon interaction signals are clearly visible as peaks above the background floor.

As is apparent from the foregoing description, various embodiments of the system of the invention may provide many advantages that can be summarized as follows:

The system is time-controlled. The system allows for a time communication between the dynamically-controllable light source and the detection means.

The system may allow for several excitation wavelengths.

Through a tunable Raman-seed light source, a Raman shift is adjustable, and hence not limited to the ordinary 13.2 THz.

The system can allow for electronically adjustable pulse width, repetition rate, repetition pattern and intensities.

All wavelengths may exit the same fiber. The geometry of the beam remains the same, chromatic errors are mostly avoided.

Multimodal measurements can be encoded sequentially in time. This way it is possible to detect signals of several imaging modalities with only one photo detector.

Even after frequency doubling, the time overlap should not be critical with typically used nanosecond pulses. No additional measures are necessary to ensure the matched timing between different wavelengths for multi-photon interactions.

The incorporated amplifying element(s) ensure(s) sufficient intensities to enable e.g. two-photon microscopy.

The systems allows to employ near-infrared light, which enables higher penetration depth as compared to Ti:Sa laser usually used.

By using several detectors or the aforementioned parallel time multiplex approach, it is further possible to record multi-modal images with a single measurement. Accordingly, the presented system is also a possible extension for existing multi-photon microscopes or might be used as a multi-photon material processing tool.

The creation of the multi-photon-excitation can be actively time-controlled, and the detection can be synchronized to this creation.

Compared to current setups, like commercially available multi-photon microscopes, the invention allows for a dramatically simplified device. The usually used complex and expensive short pulse light sources can be replaced with the dynamically-controllable light source of the present invention. Such light source is cost effective, robust and built of readily tested and reliable components. Further, the light source setup is in multiple aspects easy to use and flexible. The possibility of synchronization and flexible control allows for a time-based excitation and a time-gated detection to suppress interfering or background signals effectively. Furthermore, this allows for a time-resolved analysis of TPEF signals and fluorescence lifetimes.

It is believed that the present invention could replace expensive femtosecond light sources.

It is suspected that the dynamically-controllable light source of the present invention allows for a more biocompatible imaging, as the typically longer pulses on the nanosecond time scale could be better biocompatible because of less cell damage. Still, in spite of the longer pulse lengths, it has been demonstrated that the intensity is still sufficient for obtaining TPEF or SHG images.

Because of the fiber based architecture, an application to endoscopes is possible.

In the system of the invention, pulse patterns, repetition rate, pulse length, peak power and CW power are controllable.

In the system according to an embodiment of the invention, the wavelength is switchable: with Raman shifting and the delivery fiber from 1064 to 1022 or 1185 or further.

Further, the wavelength of the dynamically-controllable light source can be tunable within the Ytterbium-gain or within the Raman-gain of the used fiber.

While transport of femtosecond or picosecond high power pulses in fibers is difficult to achieve, in the invention the entire system is inherently fiber based.

Eligibility of the excitation wavelengths is in particular possible in view of the broad gain of the used non-linear gain media like Ytterbium-doped fiber or the Raman-gain of the glass fiber.

The active modulation allows not only for flexible adjustment of the repetition rate for the investigated sample, but also to avoid harmful triplet excitations.

While the peak power provided by the dynamically-controllable light source of the invention will of course be smaller than that of typically used femtosecond lasers, it is seen that the peak power is still sufficient for TPEF and SHG imaging. It is further facilitated by the fact that the system of the invention typically involves wavelengths longer than those of conventional TPEF microscopes where many standard fluorescence stains or dyes are available.

As mentioned before, by active modulation of the light source, the excitation detection can be synchronized. It is thus possible to acquire fluorescence lifetimes with a single excitation pulse by the applicational fast detection electronics.

Since the light source may be entirely fiber based, the delivery to remote places is possible, such as in a hand-held detector, or for excitation in an enclosed or sealed environment.

In a single mode setup, the system allows for a high spatial resolution, where in fact a diffraction limited resolution becomes possible.

The system is comparatively insensitive to environmental effects, and needs no specific cooling or calibration appliances.

The system may provide for a comprehensive spectral coverage of excitation light.

The system is typically comparatively dispersion insensitive, because of long pulses and narrow band spectrum. This allows for a simple optical setup, in which standard lenses can be used instead of expensive objectives, and no sophisticated pulse handling, like pre-chirping, is necessary.

The system allows for a high sensitivity.

A wavelength tunability provided in some embodiments enables specific excitation of single absorption bands.

The system may allow to change the applied power by choosing appropriate pulse patterns. Making the pulses longer or increasing the pulse repetition rate would lead to a lower instantaneous power of the pulses. Thus, it is possible to stay below the threshold power for a non-linear wavelength conversion and therefore suppress the wavelength conversion. This is a way to reduce the output power of a shifted wavelength signal or to even switch it off. For example, a possible realization could be to switch a Raman shifted 1122 nm light on or off by making the 1064 nm Raman pulses longer and increasing the repetition rate to lower the 1064 nm power and being below the Raman conversion threshold.

Various embodiments of the invention allow for measuring the fluorescence lifetime of the fluorophores. Note that current systems typically employ the time-correlated single-photon counting (TCSPC) method for determining fluorescence lifetimes. Herein, a suitable electronics is employed for measuring the time between the arrival of an excitation pulse and the emission of the fluorescence photon. From a plurality of such single-photon measurements, the fluorescence lifetime can be determined. To provide for a time reference, a small fraction of the excitation pulse is branched off and guided to a photodiode, which in turn generates a trigger signal for the detection unit which serves as a timing reference point.

A similar method can be applied within the framework of the invention, but the additional branched-off light portion and the additional diode for generating the trigger or start signal can be dispensed with, since in various embodiments of the invention, the generation of the excitation pulse and the detection are a priori synchronized, for example by employing a same function generator, which provides the start signal for the generation of the excitation pulse and shares the start signal with all other components.

The time difference between the stimulation/excitation pulse and the detected photon can likewise be measured with the known TCSPC electronics, but could alternatively also be determined using an oscilloscope. For this purpose, several consecutive excitation events can be digitized, and the time differences between the fluorescence photons and the reference signal can be measured. In this method, for each excitation pulse it can be determined whether only one or more fluorescence photons are detected after each pulse, and with this information, the power of the excitation light source can be adapted online. Further, using a suitable detector unit and digitization, it is even possible to distinguish several fluorescence photons per excitation pulse.

As an alternative to the digital method of measuring the fluorescence lifetime, various embodiments of the invention further allow for measuring the decay curve of a fluorophore in an analog manner. With the high pulse energies that can be provided in the framework of the invention, many fluorescence photons can be generated with a single pulse. The fluorescence signal can then be detected with a suitable detector and digitized with a fast ADC. Herein, suitable detectors have a high analog bandwidth, a high linearity and a high dynamic range. The lifetime can be derived directly from the temporal decay of the voltage signal. The decay can be corrected to account for effects or artefacts of the detection unit.

Further, in some embodiments, the measurement of the fluorescence can be carried out with a time resolution that is higher than the sample rate of the ADCs of the detector. This can be achieved by varying a time delay between the start pulse and the trigger signal by less than a sample time of the ADC, such that different sequences of measurements can be interleaved in time. The time resolution of the measurement is then limited by the length of the excitation pulse, which can be as low as e.g. 10 ps, or limited by the possibilities of adjusting the arbitrary waveform generator.

In order to measure the lifetime of the fluorophores, it is necessary to correlate each fluorescence photon with the corresponding stimulation event. It can be assumed that after a time which is considerably longer than the fluorescence lifetime, no fluorescence photons will occur any more. However, if the time between two excitation pulses is similar to the lifetime of the fluorophore to be examined, the decay curves can overlap, which makes the exact determination of the lifetime more difficult. However, in various embodiments of the invention, it is easily possible to adjust the rate of the excitation pulses.

Further, the repetition rate can even be adjusted such that comparatively long-lived triplet states can be accounted for. The lifetime of the triplet states can be as long as several milliseconds. The system can then be controlled such that in this period of time, no further excitation pulse occurs. In case of lifetimes of 100 ps, or 1 ns or even 10 ns, a repetition rate of less than 10 MHz, preferably less than 1 MHz, and even more preferably less than 100 kHz can be selectively chosen. The pulse lengths can likewise be selectively adjusted, for example increased from 10 ps up to 100 ps, or preferably 1 ns, or even longer.

For generating different excitation wavelengths, in various embodiments an optical parametric oscillator (OPO) can be employed which generates an idler light and a signal light from an input light signal. Such OPOs are commonly used in femtosecond systems in order to tune the wavelength over a broader range as permitted by the laser medium. However, unfortunately, such OPOs are extremely susceptible to perturbation or errors when used with such short pulses. However, when using excitation pulses on the nanosecond timescale, as is the case in embodiments of the present invention, OPOs operate much more reliably than for femtosecond pulses. OPOs employ an optically non-linear crystal in an optical resonator. In combination with ordinary femtosecond light sources, the wavelengths of the idler and signal radiations are then changed by changing the orientation of the crystal. However, in the framework of the present invention, instead of turning the crystal, the wavelength of the input light generated by the dynamically controllable light source can be changed, which is simpler and more robust than manipulating the crystal. This is particularly advantageous if later on a sum frequency generation (SFG) or difference frequency generation (DFG) shall be accomplished.

In a preferred embodiment, the modulation ratio of the seed light source should be better than 30 dB, preferably better than 40 dB, and most preferably better than 50 dB. In order to obtain a high modulation ratio, different strategies can be applied. One solution is to operate the seed light source in the CW mode and to modulate the light afterwards using a suitable modulator. Herein, EOMs reach modulation depths of 20 dB to 30 dB. For further improvement, the seed light source can be pre-modulated.

In some embodiments, the seed light source for the MOPA-setup can already be operated with the desired modulation pattern, e.g. for generating pulses in a range from 10 ps to 10 ns, when a suitable seed light source and a suitable electrical driver are chosen. Suitable light sources are, for example, DFB diodes, VCSELs, external cavity diode lasers, Q-switched diode lasers, FBG-stabilized laser diodes and other semiconductor-based laser diodes. Particularly preferred are laser diodes with a close-to-chip Fiber Bragg Grating (FBG).

In order to maximize the light power of the fiber laser, it is preferable to properly choose the length of the fiber behind the power amplifier. The length of the passive fiber after the last active fiber should not be longer than 10 m, and is preferably less than 6 m, and most preferably less than 2 m.

Many optical elements have different behavior for different polarizations of the incoming light. In order to control this behavior, it may be necessary to adjust the polarization of the light from the laser. For this purpose, fiber-based polarization controllers can be used. Since the polarization may also change due to temperature changes, in some embodiments the polarization is measured using a polarization analyzer and the polarization is controlled according to an optimal operation point using feedback control. In the alternative, the fiber laser can be of a polarization maintaining design, employing polarization maintaining components in all or part thereof.

Typical excitation laser systems are devised for a certain optical power. In order to adjust the optical power that is applied to the sample, typically the power is adjusted after the laser. In contrast to this, according to various embodiments of the present invention, the output power can be directly controlled via the pump power. Herein, it is especially advantageous that the pump power can be adjusted very quickly, allowing the power to be adapted even during a measurement to changing conditions. This is particularly important for the measurement of fluorescence lifetimes, since the excitation power plays a crucial role for the quality of the result. For example, in TCSPC, too high excitation powers can lead to a misinterpretation of the photon events, for example in cases where only a single fluorescence photon can be measured per excitation pulse, and photons arriving later than this event remain unnoticed.

The invention claimed is:

1. A system for inducing and detecting multi-photon processes in a sample, said system comprising:
   a dynamically-controllable light source, said dynamically-controllable light source comprising
      a first sub-light source, said first sub-light source being electrically controllable such as to generate controllable time-dependent intensity patterns of light having a first wavelength, and
      at least one optical amplifier,
   thereby allowing for active time-control of creation of multi-photon-excitation,
   a beam delivery unit for delivering light generated by said dynamically-controllable light source to a sample site, and
   a detector unit or detector assembly for detecting signals indicative of said multi-photon process.

2. The system of claim 1, wherein said dynamically-controllable light source is a narrow-band coherent dynamically-controllable light source.

3. The system of claim 1, wherein the dynamically-controllable light source and the detector unit/assembly are adapted to communicate or share timing, time control, or time sensing information in at least one direction by one or more of
   a trigger signal exchanged at least in one direction,
   sharing the same time gate or a sample clock,
   synchronizing or phase-locking electrical signals involved in the time control of the dynamically-controllable light source and the detector unit/assembly.

4. The system of claim 1, further comprising a time control unit for controlling one or both of the dynamically-controllable laser and the detection unit/assembly.

5. The system of claim 1, wherein the system comprises an electronic function generator generating electronic signals for operation of one or both of the dynamically-controllable light source and the detector unit/assembly, wherein the electronic function generator is synchronized with the dynamically-controllable light source.

6. The system of claim 1, wherein the system is part of an endoscope, an OCT device, a light microscope, a photo-acoustic imaging device, a Raman spectrometer or an ultrasonic imaging device.

7. The system of claim 1, said system comprising a device for scanning different sample locations, wherein the device for scanning different sample locations comprises one or more of:
   one or more moving mirrors for deflecting light from said dynamically-controllable light source to a predetermined sample location or one or more mirrors for deflecting the light reflected from a sample location,
   a device for scanning an optical fiber or a fiber bundle carrying light of said dynamically-controllable light source with respect to a sample, or
   a device for scanning the sample relative to the light signal,
   wherein the time control of the dynamically-controllable light source and the scanning device are adapted to communicate or share timing, time control or time sensing information in at least one direction by one or more of
   exchanging trigger signals in at least one direction,
   sharing common electrical signals, and
   synchronizing the control of the light source and the scanning device.

8. The system according to claim 1, wherein the system is further adapted for fluorescence lifetime imaging.

9. The system according to claim 1, wherein said beam delivery unit comprises an optical fiber, wherein at least 80% of the light path between the dynamically-controllable light source and the sample site is located in said optical fiber.

10. The system according to claim 1, wherein the detector unit/assembly comprises at least one photo detector, wherein the output signal of said photo detector is connected to an analog-digital-converter, wherein the signal detection by means of the analog-digital-converter is synchronized with the dynamically-controllable light source.

11. The system of claim 1, wherein the beam delivery unit comprises a single mode core of a double clad fiber, and in which signals generated by or indicative of said multi-photon process are guided through the multi-mode cladding to the detector unit/assembly, and
   further comprising one or more dichroic filters, or other wavelength selective elements to separate the light signal for inducing multi-photon processes and the light signal generated by or indicative of said multi-photon process from each other.

12. The system according to claim 1, wherein the system is a device for multi-modal measurements combining the measurement of the multi-photon processes with at least one other measurement modality selected from a group consisting of microscopes, confocal microscopes, OCT, Raman spectroscopy and different modes of multi-photon processes, wherein the multi-modal measurements are encoded sequentially in time, thereby allowing to detect different measurement or imaging modes with the same detector unit/assembly.

13. The system according to claim 1, wherein the operation of the dynamically-controllable light source and the detector unit/assembly is time-controlled such that different detection or imaging modalities are employed in a time-multiplexed manner, of which at least one modality involves multi-photon processes,
   wherein the modalities include one or more of two photon excited fluorescence, second harmonic generation, third harmonic generation and confocal microscopy.

14. The system of claim 1, further comprising:
a Raman active medium suitable to cause Raman scattering of light having said first wavelength,
a second sub-light source capable of emitting light with a second wavelength, said second wavelength being longer than said first wavelength, and
an optical fiber or wave guide, wherein said light emitted by said first and second sub-light sources traverses a length of said optical fiber or wave guide in a feed-forward configuration to facilitate a non-linear wavelength conversion step involving said Raman-active medium,
wherein at least one of said first and second sub-light sources has a coherence length longer than 0.05 mm.

15. The system of claim 14, wherein the wavelength converted light resulting from said wavelength conversion step has a coherence length longer than 0.05 mm.

16. The system of claim 14, further comprising a modulator for modulating light generated by the first or second sub-light source, wherein said modulator is one of
an electro-optical modulator,
an acoustic-optical modulator, or
a swept Fabry-Pérot filter,
and wherein said modulator can be electronically controlled to generate one or more of:
a CW light signal
a periodic sinusoidal modulation or
a light pulse pattern.

17. The system of claim 16, wherein the pulse lengths of the light pulse pattern are at least 10 ps, and 50 ns or below, and wherein the modulator can be electronically controlled to configure the time delay between each two consecutive pulses with a mean repetition rate of 10 kHz or more.

18. The system of claim 14, wherein the Raman active medium is formed by an optical fiber, wherein the length of the fiber can be selected such as to allow for two or more consecutive Raman wavelength shifts.

19. The system of claim 1, wherein said first sub-light source has a wavelength of 950 nm to 1200 nm, or a wavelength of 1450 to 1700 nm, and wherein said dynamically-controllable light source is operable with a duty cycle of less than 10%.

20. The system of claim 1, wherein the instantaneous power of the dynamically-controllable light source is more than 10 W.

* * * * *